(12) United States Patent
Pack-Walden et al.

(10) Patent No.: US 7,806,267 B2
(45) Date of Patent: Oct. 5, 2010

(54) ARTICLES SUITABLE FOR USE AS A MEDICAL DEVICE COVER AND METHODS OF MAKING AND USING THE SAME

(75) Inventors: Ginger Carol Pack-Walden, Columbus, MS (US); Mark S. Dillon, Columbus, MS (US); David Alan Daugherty, Columbus, MS (US)

(73) Assignee: Microtek Medical, Inc., St. Paul, MN (US)

( * ) Notice: Subject to any disclaimer, the term of this patent is extended or adjusted under 35 U.S.C. 154(b) by 482 days.

(21) Appl. No.: 11/879,709

(22) Filed: Jul. 18, 2007

(65) Prior Publication Data
US 2009/0020357 A1    Jan. 22, 2009

(51) Int. Cl.
*A61B 19/02* (2006.01)

(52) U.S. Cl. ............... 206/438; 206/363; 206/390; 181/131

(58) Field of Classification Search ............ 206/438, 206/363, 390, 554, 484, 370; 181/131, 130; 221/282, 283, 69, 70; 600/528; 428/906; 383/37
See application file for complete search history.

(56) References Cited

U.S. PATENT DOCUMENTS 3,109,474 A * 11/1963 Levi ..................... 150/158
4,677,697 A * 7/1987 Hayes ..................... 2/159
4,773,532 A * 9/1988 Stephenson ............ 206/278
4,802,550 A * 2/1989 Poore ..................... 181/131
4,849,090 A * 7/1989 Case et al. .............. 206/390
4,871,046 A * 10/1989 Turner .................... 181/131
5,486,659 A    1/1996 Rosenbush
5,819,739 A * 10/1998 Levavi et al. ........... 600/499
5,971,138 A * 10/1999 Soughan ................. 206/210
6,168,019 B1 * 1/2001 Olson ..................... 206/390
6,186,957 B1 * 2/2001 Milam .................... 600/528
6,467,568 B1 * 10/2002 Kemper .................. 181/131
6,575,917 B2 * 6/2003 Giroux et al. ........... 600/528
7,117,971 B1 * 10/2006 Cornacchia ............. 181/131
7,322,135 B2 * 1/2008 Gulati ..................... 40/316
2002/0170771 A1 * 11/2002 Milam et al. ............ 181/131

FOREIGN PATENT DOCUMENTS

WO    WO 96/22043    7/1996

* cited by examiner

*Primary Examiner*—Jila M Mohandesi
*Assistant Examiner*—Steven A. Reynolds
(74) *Attorney, Agent, or Firm*—Andrew D. Sorensen; Laura C. Dilorenzo

(57) ABSTRACT

Article suitable for use as a medical device cover are disclosed. Methods of making and using the articles are also disclosed.

10 Claims, 5 Drawing Sheets

ARTICLES SUITABLE FOR USE AS A MEDICAL DEVICE COVER AND METHODS OF MAKING AND USING THE SAME

FIELD OF THE INVENTION

The present invention relates generally to articles suitable for use as a protective cover, such as a stethoscope cover; methods of making the articles; and methods of using the articles.

BACKGROUND OF THE INVENTION

Due to growing concerns regarding the transmission of germs and/or particulate material from one patient to another patient or from a first patient to a piece of medical equipment and then to a second patient, efforts continue in the design protective articles, such as stethoscope covers, to further enhance the safety profile of medical devices such as stethoscopes.

There is a need in the art for articles that (i) provide superior barrier protection between a piece of medical equipment, such as a stethoscope, and a patient during use, (ii) are designed to be easily operational, (iii) are disposable after use, or (iv) any combination of (i) to (iii).

SUMMARY OF THE INVENTION

The present invention is directed to an article suitable for providing temporary protection to an object that is insertable into a sleeve of the article (i.e., also referred to herein as "an insertable object"). The articles of the present invention provide one or more of the following features: (i) superior barrier protection between an insertable object, such as a stethoscope, and a patient during use, (ii) disposability after use, and (iii) ease of operation for the user (e.g., a doctor).

According to one exemplary embodiment of the present invention, the article comprises a roll of sleeves comprising two or more sleeves that are (i) connected to one another, and (ii) separated from one another via at least one line of perforations that enables the two or more sleeves to be separated from one another along the at least one line of perforations, each sleeve having a sleeve opening positioned along a length of the sleeve, the sleeve opening providing access to a cavity within the sleeve, the cavity being operatively adapted to surround at least a portion of an insertable object. The exemplary article may further comprise a number of additional components including, but not limited to, a housing for the roll of sleeves, the housing comprising a first slot sized so that at least an end portion of a sleeve can extend therethrough; a bracket for suspending the roll of sleeves within the housing; a rod operatively adapted to (i) extend through the roll of sleeves, and (ii) attach to the bracket along opposing ends of the rod; one or more attachment members operatively adapted to attach the roll of sleeves to another object, such as a stethoscope; or any combination thereof.

According to a further exemplary embodiment of the present invention, the article comprises a sleeve comprising (a) two film portions joined to one another (i) along at least one edge extending along a sleeve length and (ii) along opposite edges extending along a sleeve width, and (b) a sleeve opening that extends across the sleeve width and is positioned at a location along the sleeve length between the opposite edges, the sleeve opening being sized so that at least a portion of an insertable object, such as a stethoscope bell, can extend therethrough and into a cavity surrounded by the two film portions. The exemplary article may further comprise a number of additional components including, but not limited to, a housing for the sleeve, the housing comprising a first slot sized so that at least an end portion of the sleeve can extend therethrough; a bracket for suspending a roll of sleeves within the housing; a rod operatively adapted to (i) extend through a roll of sleeves, and (ii) attach to the bracket along opposing ends of the rod; one or more attachment members operatively adapted to attach the sleeve or roll of sleeves to another object, such as a stethoscope; or any combination thereof.

According to another exemplary embodiment of the present invention, the article comprises a roll of sleeves comprising two or more sleeves that are (i) connected to one another, and (ii) separated from one another via at least one line of perforations that enables the two or more sleeves to be separated from one another along the at least one line of perforations, each sleeve being operatively adapted to surround at least a portion of an insertable object; a housing for the roll of sleeves, the housing comprising a first slot sized so that at least an end portion of a sleeve can extend therethrough; a bracket for suspending the roll of sleeves within the housing; a rod operatively adapted to (i) extend through the roll of sleeves, and (ii) attach to the bracket along opposing ends of the rod; and one or more attachment members operatively adapted to attach the roll of sleeves to another object.

The present invention is also directed to a stethoscope cover assembly comprising at least one of the above-described articles in combination with a stethoscope. In one exemplary embodiment, the stethoscope cover assembly comprises (I) an article comprising a sleeve comprising (a) two film portions joined to one another (i) along at least one edge extending along a sleeve length and (ii) along opposite edges extending along a sleeve width, and (b) a sleeve opening that extends across the sleeve width and is positioned at a location along the sleeve length between the opposite edges, the sleeve opening being sized so that at least a portion of a stethoscope bell can extend therethrough and into a cavity surrounded by the two film portions, and (II) a stethoscope.

The present invention is further directed to methods of making articles. In one exemplary embodiment of the present invention, the method of making an article comprises forming a sleeve comprising two film portions joined to one another (i) along at least one edge extending along a sleeve length and (ii) along opposite edges extending along a sleeve width, and providing a sleeve opening through one of the two film portions so that the sleeve opening extends across the sleeve width and is positioned at a location along the sleeve length between the opposite edges, the sleeve opening being sized so that at least a portion of an insertable object, such as a stethoscope bell, can extend therethrough and into a cavity surrounded by the two film portions.

In a further exemplary embodiment of the present invention, the method of making an article comprises forming a roll of sleeves comprising two or more sleeves that are (i) connected to one another, and (ii) separated from one another via at least one line of perforations that enables the two or more sleeves to be separated from one another along the at least one line of perforations, each sleeve having a sleeve opening positioned along a length of the sleeve, the sleeve opening providing access to a cavity within the sleeve, the cavity being operatively adapted to surround at least a portion of an insertable object, such as a stethoscope bell.

The present invention is even further directed to methods of using an article to temporarily cover or protect an insertable article such as a piece of medical equipment. In one exemplary embodiment of the present invention, the method of using an article comprises inserting at least a portion of a medical instrument within a cavity of a sleeve while the sleeve is connected to a roll of sleeves so as to form a covered medical instrument; utilizing the covered medical instrument for an intended purpose; and, after the utilizing step, separating the sleeve from the roll of sleeves by tearing along at least one line of perforations.

In another exemplary embodiment of the present invention, the method comprises providing an article such as one of the above-described articles; attaching the article to a stethoscope; positioning a stethoscope bell within a first sleeve so as to form a covered stethoscope bell; and contacting a first patient with a portion of the covered stethoscope bell. The exemplary method may further comprise removing the stethoscope bell from the first sleeve; positioning the stethoscope bell within a second sleeve so as to form a covered stethoscope bell; and contacting a second patient with a portion of the covered stethoscope bell.

These and other features and advantages of the present invention will become apparent after a review of the following detailed description of the disclosed embodiments and the appended claims.

BRIEF DESCRIPTION OF THE FIGURES

The present invention is further described with reference to the appended figures, wherein.

DETAILED DESCRIPTION OF THE INVENTION

The present invention is directed to articles alone or in combination with an insertable object, such as a stethoscope. The present invention is further directed to methods of making articles and methods of using articles. The articles of the present invention provide a barrier between an insertable object, such as a medical device (e.g., a stethoscope bell) and a patient so as to prevent possible contamination of the insertable object during use.

Figure 1:
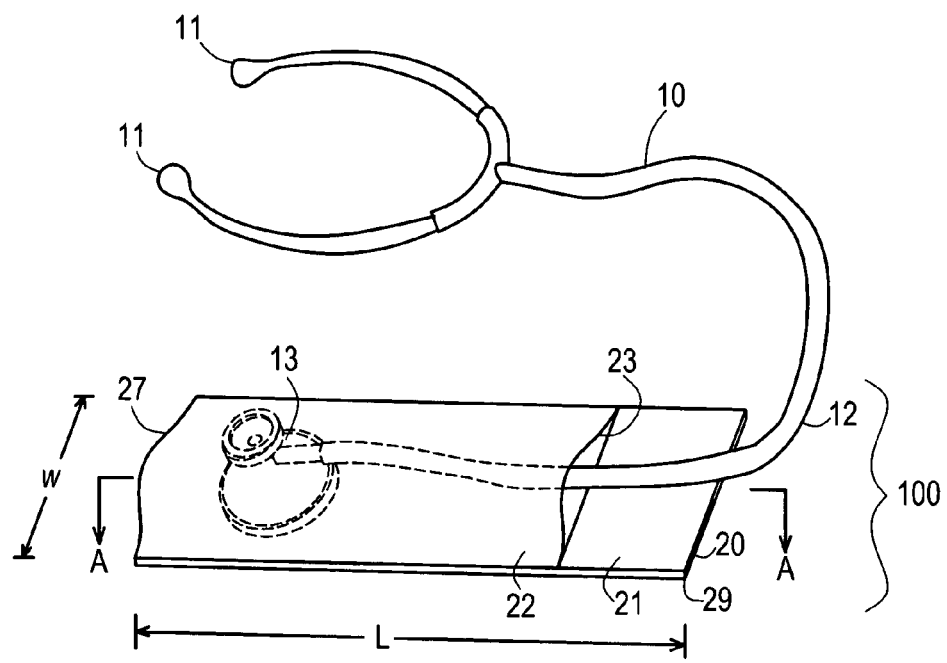
FIG. 1 depicts a frontal view of an exemplary article of the present invention in combination with a stethoscope.

One exemplary article of the present invention is shown in FIG. 1. As shown in FIG. 1, exemplary article 100 comprises a sleeve 20 suitable for covering portions of a stethoscope 10, especially a stethoscope bell 13 and a portion of stethoscope tubing 12 positioned away from stethoscope ear contacts 11. Exemplary sleeve 20 comprises film portion 21 and film portion 22 separated by sleeve opening 23. As shown in FIG. 1, sleeve opening 23 extends across a sleeve width, w, of sleeve 20 and is positioned at a location along a sleeve length, L, between opposite edges (e.g., ends) 27 and 29. Sleeve opening 23 is sized so that at least a portion of a stethoscope bell 13 can extend therethrough and into a cavity 32 surrounded by two film portions 22 and 28 (see, for example, cavity 32 surrounded by two film portions 22 and 28 shown in FIG. 2).

Figure 2:
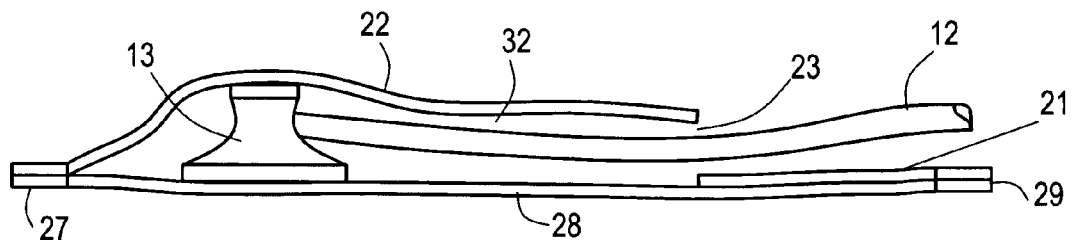
FIG. 2 depicts a cross-sectional view of the exemplary article and stethoscope shown in FIG. 1 along line A-A as shown in FIG. 1.

FIG. 2 provides a cross-sectional view of exemplary article 100 and stethoscope 10 shown in FIG. 1 along line A-A as shown in FIG. 1. As shown in FIG. 2, stethoscope bell 13 and a portion of stethoscope tubing 12 are positioned within cavity 32 formed by film portions 22 and 28. Sleeve opening 23 provides access to cavity 32. Further, as shown in FIG. 2, sleeve opening 23 is positioned at a location along sleeve length L between opposite edges 27 and 29. In this exemplary embodiment, sleeve opening 23 extends through one of two film portions (e.g., sleeve opening 23 extends through an upper film portion represented by film portions 21 and 22, but not through lower film portion 28) and is positioned within an upper half of sleeve 20 (i.e., upper film portion 21 has a film length less than that of upper film portion 22).

Figure 3:
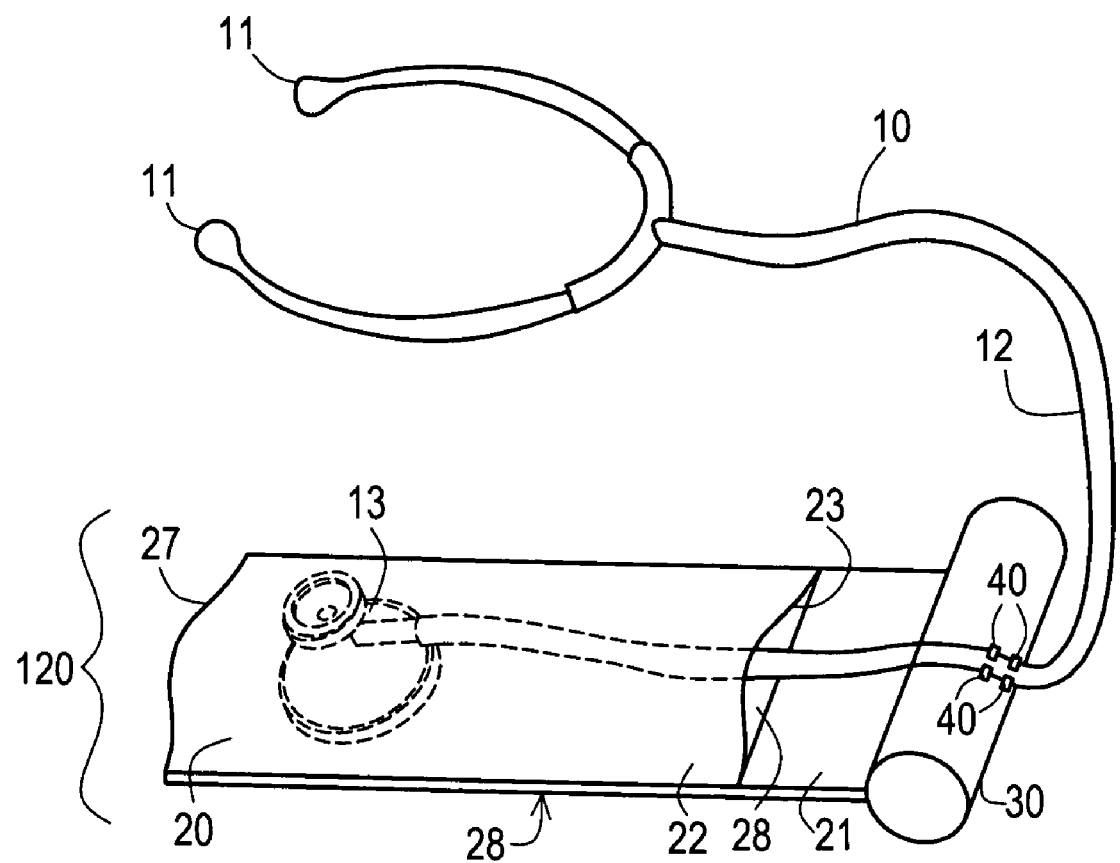
FIG. 3 depicts a view of another exemplary article of the present invention in combination with a stethoscope.

Another exemplary article of the present invention is shown in FIG. 3. As shown in FIG. 3, exemplary article 120 comprises a sleeve 20 suitable for covering an insertable object, such as stethoscope bell 13 and a portion of stethoscope tubing 12 positioned away from stethoscope ear contacts 11. Exemplary article 120 further comprises housing 30 from which sleeve 20 may extend, and attachment members 40, which are operatively adapted to attach housing 30 (and its contents, e.g., a roll of sleeves (not shown)) to another object such as stethoscope tubing 12.

As shown in FIG. 3, exemplary sleeve 20 also comprises upper film portion 21, upper film portion 22, sleeve opening 23, lower film portion 28, and opposite edges 27 and 29. Sleeve opening 23 is again sized so that at least a portion of an insertable object, such as stethoscope bell 13, can extend therethrough and into cavity 32 surrounded by film portions 22 and 28 (see, cavity 32 in FIG. 2). As shown in FIG. 3, an insertable object, such as stethoscope bell 13, typically extends through less than a complete length of a given sleeve (e.g., exemplary sleeve 20). In particular, an insertable object, such as stethoscope bell 13, typically extends into and through cavity 32 surrounded by film portions 22 and 28 but does not extend through a portion of exemplary sleeve 20 bound by film portions 21 and 28 as shown in FIG. 3.

As shown in FIGS. 1 and 3, the articles of the present invention may comprise a number of components. A description of the various components is provided below.

I. Articles of Manufacture

The articles of the present invention may comprise one or more of the following components.

A. Sleeves

The articles of the present invention may comprise one or more sleeves such as exemplary sleeve 20 shown in FIGS. 1-3. In one desired embodiment, the articles of the present invention comprise a roll of sleeves comprising two or more sleeves that are (i) connected to one another, and (ii) separated from one another via at least one line of perforations that enables the two or more sleeves to be separated from one another along the at least one line of perforations, each sleeve having a sleeve opening positioned along a length of the sleeve, the sleeve opening providing access to a cavity within the sleeve, the cavity being operatively adapted to surround at least a portion of an insertable object (e.g., stethoscope bell 13 shown in FIGS. 1-3). One exemplary roll of sleeves is shown in FIG. 4.

Figure 4:
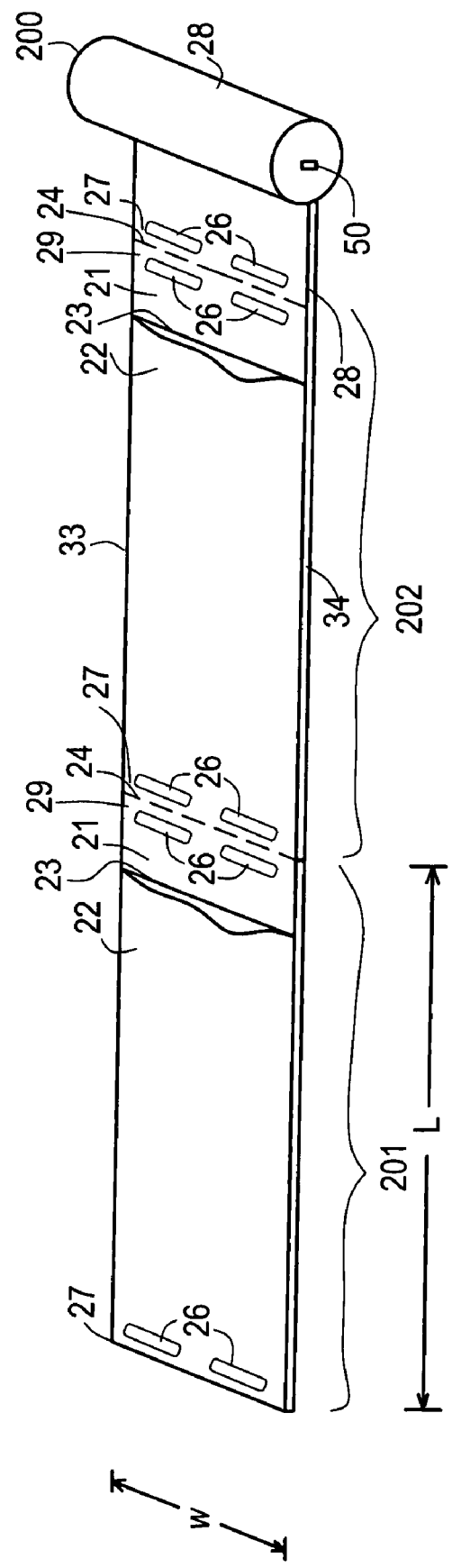
FIG. 4 depicts a view of an exemplary roll of sleeves used to form the exemplary article shown in FIG. 3.

As shown in FIG. 4, exemplary roll of sleeves 200 comprises sleeves 201 and 202 separated from one another via a line of perforations 24 that enables sleeves 201 and 202 to be separated from one another along the line of perforations 24. Each sleeve (e.g., sleeves 201 and 202) of exemplary roll of sleeves 200 comprises at least two film portions 22 and 28 joined to one another along at least one edge 33 and/or 34 extending along sleeve length L, and sleeve opening 23 that extends along sleeve width w and is positioned at a location along sleeve length L. Each sleeve opening 23 is sized so that at least a portion of an insertable object, such as stethoscope bell 13, can extend therethrough and into a cavity (e.g., cavity 32 shown in FIG. 2) surrounded by the two film portions 22 and 28. As shown in FIG. 4, each sleeve (e.g., sleeves 201 and 202) of exemplary roll of sleeves 200 comprises film portions 21, 22 and 28, which are joined to one another along opposite edges 27 and 29 extending along sleeve width w. Exemplary sleeves 201 and 202 comprise bond areas 26 extending along sleeve width w so as to bond upper film portions 21 and 22 to lower film portion 28. Bond areas 26 may extend completely along sleeve width w so as to completely seal edges 27 and 29 of each sleeve (e.g., sleeves 201 and 202) or may partially seal edges 27 and 29 of each sleeve (e.g., sleeves 201 and 202) as shown in FIG. 4. (i.e., bond areas 26 do not extend the complete sleeve width w).

Sleeve opening 23 of each sleeve (e.g., sleeves 201 and 202) may extend completely across sleeve width w from first edge 33 extending along sleeve length L to second opposite edge 34 extending along sleeve length L as shown in FIG. 4 or less than the complete sleeve width w. Sleeve opening 23 of each sleeve (e.g., sleeves 201 and 202) may be positioned at any location along sleeve length L, but is desirably within an upper half of each sleeve (e.g., sleeves 201 and 202) as shown in FIG. 4, wherein the upper half is positioned between the roll of sleeves 200 and a lower half of a given sleeve (e.g., sleeve 202).

Each sleeve (e.g., sleeves 201 and 202) of exemplary roll of sleeves 200 typically has a sleeve length L ranging from about 6.0 inches (in) (15.2 centimeters (cm)) to about 18 in (45.7 cm), more desirably, from about 10 in (25.4 cm) to about 14 in (35.6 cm); a sleeve width w ranging from about 2.0 in (5.1 cm) to about 6.0 in (15.2 cm), more desirably, from about 2.5 in (6.4 cm) to about 4.0 in (10.2 cm); and a sleeve opening 23 positioned from about 0.0 in (0.0 cm) to about 6.0 in (15.2 cm), more desirably, from about 1.0 in (2.5 cm) to about 4.0 in (10.2 cm) from an edge (e.g., edge 29) of the sleeve. In one exemplary embodiment, each sleeve (e.g., sleeves 201 and 202) of exemplary roll of sleeves 200 has a sleeve length L of about 12.5 in (31.8 cm), a sleeve width w of about 3.0 in (7.6 cm), and a sleeve opening 23 positioned about 2.5 in (6.4 cm) from an edge (e.g., edge 29) of the sleeve.

Film portions 21, 22 and 28 may comprise any film-forming material. Suitable film-forming materials include, but are not limited to, polyolefins such as polyethylene, polypropylene ethylene-containing copolymers (e.g., ethylene methyl acrylate or EMA) and propylene-containing copolymers, polyesters, polyvinyl alcohol, or combinations thereof. Desirably, film portions 21, 22 and 28 comprise transparent or translucent film-forming material such as polyethylene, polypropylene, EMA or similar polymers. Typically, film portions 21 and 22 comprise a single film that has been cut in order to provide sleeve opening between film portions 21 and 22. Further, in some embodiments, film portions 21, 22 and 28 may comprise a single tubular film that is flattened, and then cut in order to provide sleeve opening between film portions 21 and 22. Typically, film portions 21, 22 and 28 have a film thickness of less than about 10 mils (254 μm), more typically, from about 1.0 mil (25.4 μm) to about 5.0 mils (127 μm). In one exemplary embodiment, film portions 21, 22 and 28 have a film thickness of about 3.0 mils (76.2 μm).

B. Housing

Figure 5:
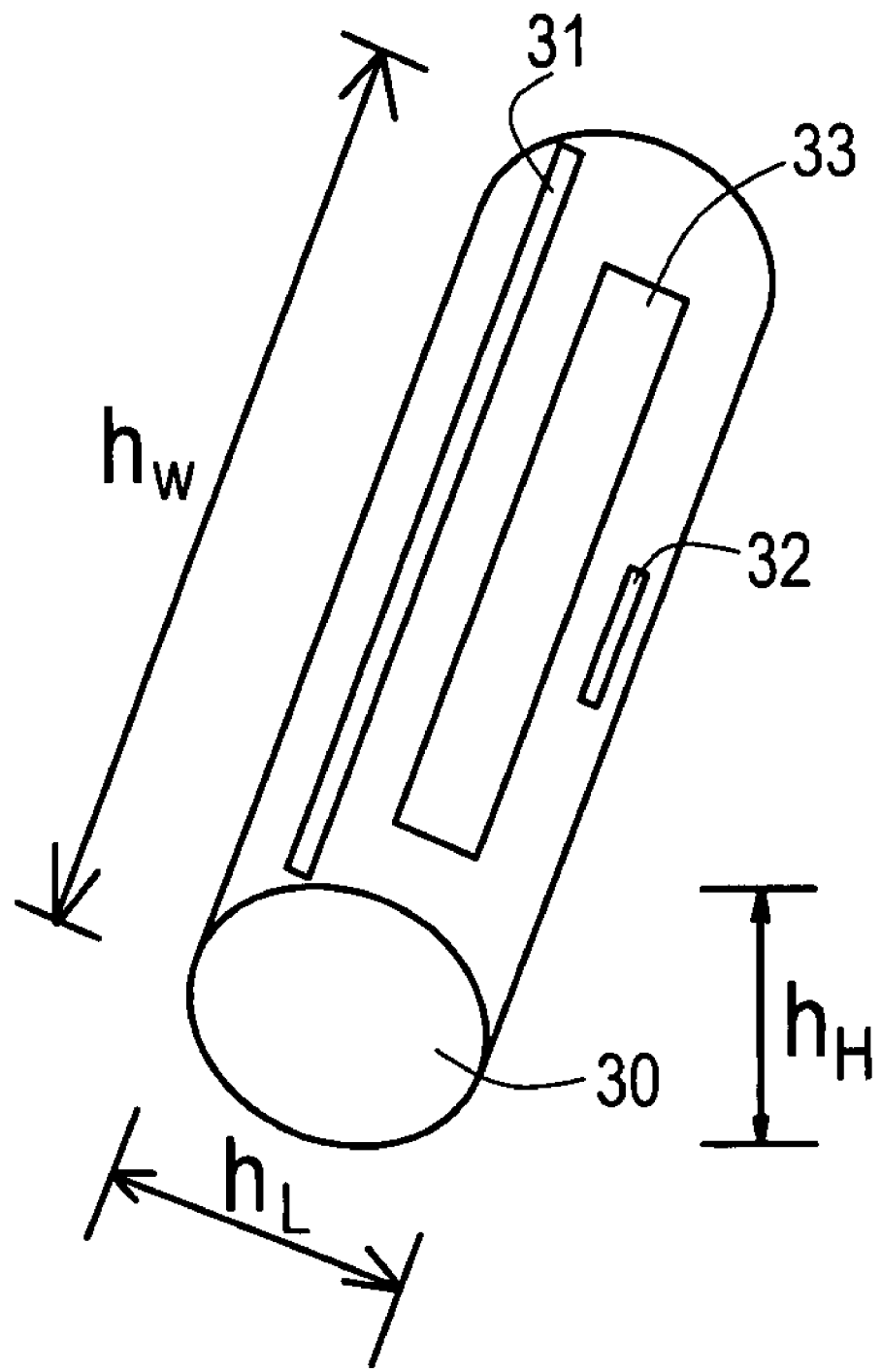
FIG. 5 depicts a view of an exemplary housing used to form the exemplary article shown in FIG. 3.

The articles of the present invention may further comprise a housing such as exemplary housing 30 shown in FIGS. 3 and 5. Housing 30 may be sized to encompass a single sleeve, such as sleeve 20 shown in FIGS. 1-3, or a roll of sleeves, such as exemplary roll of sleeves 200 shown in FIG. 4. Desirably, housing 30 is sized so as to encompass a roll of sleeves, such as exemplary roll of sleeves 200 shown in FIG. 4.

As shown in FIG. 5, exemplary housing 30 comprises a first slot 31 sized so that at least an end portion of a sleeve (e.g., sleeve 20 or sleeve 201) can extend therethrough. Typically, first slot 31 extends across a full housing width $h_w$, although first slot 31 may extend less than the complete housing width $h_w$ so long as a given sleeve (e.g., sleeve 20 or sleeve 201) can extend through first slot 31. Exemplary housing 30 may further comprise one or more second slots 32 sized so that at least a portion of each attachment member (e.g., attachment members 40 shown in FIG. 3) can extend therethrough.

Each of the one or more second slots 32 is sized slightly greater than the cross-sectional dimensions of a given attachment member (e.g., attachment member 40 shown in FIG. 3). Typically, each of the one or more second slots 32 has (i) a slot width (e.g., a dimension extending parallel with housing width $h_w$) ranging from about 0.25 in (0.6 cm) to about 1.0 in (2.5 cm), more typically, from about 0.5 in (1.3 cm) to about 0.8 in (2.0 cm), and (ii) a slot depth (e.g., a dimension extending perpendicular to housing width $h_w$) ranging from about 0.05 in (1.3 millimeters (mm)) to about 0.2 in (5.1 mm).

Exemplary housing 30 typically has a housing width $h_w$ with a width dimension slightly greater than sleeve width w described above. For example, when sleeve width w is about 3.0 in (7.6 cm), housing width $h_w$ typically ranges from about 3.2 in (8.1 cm) to about 4.0 in (10.2 cm), and first slot 31 extends a length of from about 3.0 in (7.6 cm) to about 3.2 in (8.1 cm). Further, exemplary housing 30 has (i) a housing length $h_L$ and (ii) a housing height $h_H$, each of which can vary as desired so as to encompass a desired number of sleeves. Typically, each of housing length $h_L$ and housing height $h_H$ ranges from about 0.5 in (12.7 cm) to about 3.0 in (76.2 cm), more typically, from about 1.0 in (25.4 cm) to about 1.5 in (38.1 cm).

Housing 30 may comprise a variety of materials. Suitable materials include, but are not limited to, film-forming materials such as those described above or polyvinyl chloride (PVC), fabric materials (e.g., woven, nonwoven, and knit materials), metal foils, or combinations thereof. Desirably, housing 30 comprise a film-forming material such as polyethylene, polypropylene or PVC.

As shown in FIG. 5, exemplary housing 30 may further comprise a label or indicia 33. Optional label or indicia 33 may be used to distinguish a given housing (e.g., Dr. Smith's housing) from another housing (e.g., Dr. Jone's housing).

C. Bracket

Figure 6A:
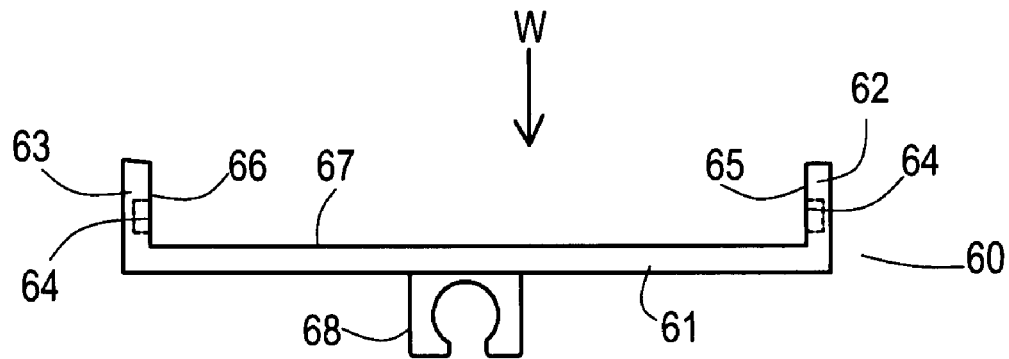
FIG. 6A depicts a side view of an exemplary bracket used to form the exemplary article shown in FIG. 3.
Figure 6B:
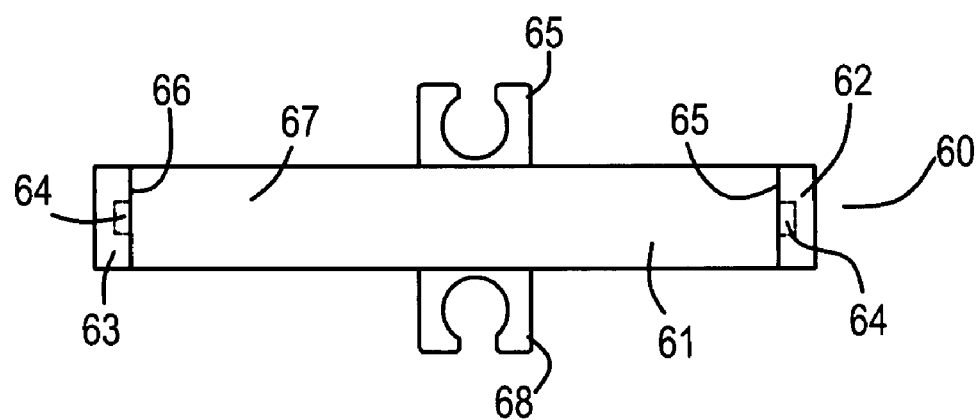
FIG. 6B depicts a top view of the exemplary bracket shown in FIG. 5A along direction W as shown in FIG. 5A.

The articles of the present invention may further comprise a bracket for suspending a roll of sleeves within a housing, such as exemplary bracket 60 shown in FIGS. 6A-6B. Bracket 60 may be sized to support a single sleeve, such as sleeve 20 shown in FIGS. 1-3, or a roll of sleeves, such as exemplary roll of sleeves 200 shown in FIG. 4. Desirably, bracket 60 is sized so as to support a roll of sleeves, such as exemplary roll of sleeves 200 shown in FIG. 4.

As shown in FIGS. 6A-6B, exemplary bracket 60 comprises a central member 61 that connects upwardly extending end members 62 and 63. Each of upwardly extending end members 62 and 63 comprise an indentation 64 positioned along an inner surface of end members 62 and 63 (e.g., inner surfaces 65 and 66). Indentations 64 are operatively adapted so as to accept an end portion of a rod extending through a roll of sleeves (see, for example, rod 50 through roll of sleeves 200 shown in FIG. 4).

Central member 61 and end members 62 and 63 have dimensions suitable for supporting a roll of sleeves within a volume of space located between an upper surface 67 of central member 61 and opposing inner surfaces 65 and 66 of end members 62 and 63 respectively. For example, when sleeve width w is about 3.0 in (7.6 cm), end members 62 and 63 are spaced from one another by about 3.2 in (8.1 cm). Further, the position of indentations 64 along opposing inner surfaces 65 and 66 of end members 62 and 63 may vary from a lower position to a higher position above upper surface 67 of central member 61 as necessary to accommodate a given roll of sleeves (i.e., for larger rolls of sleeves, indentations 64 along opposing inner surfaces 65 and 66 of end members 62 and 63 are further away from upper surface 67 of central member 61).

As shown in FIGS. 6A-6B, exemplary bracket 60 may further comprise one or more attachment members 65. In this exemplary embodiment, attachment members 65 are integrally attached to and extend outwardly from central member 61. Attachment members 65 are operatively adapted to attach exemplary bracket 60 (and the roll of sleeves attached thereto) to another object, such as stethoscope tubing (e.g., stethoscope tubing 12 shown in FIGS. 1-3).

Exemplary bracket 60 may comprise a variety of materials. Suitable materials include, but are not limited to, thermoformable materials such as the film-forming materials described above, polyurethanes, acrylonitrile-butadiene-styrene (ABS) copolymers, polyethylene terephthalate glycol (PETG), polyamides, etc. Desirably, exemplary bracket 60 comprises a thermoformed part comprising polypropylene or an ABS copolymer.

D. Rod

As discussed above, the articles of the present invention may further comprise a rod such as exemplary rod 50 shown in FIG. 4. Exemplary rod 50 is operatively adapted to (i) extend through a roll of sleeves (e.g., roll of sleeves 200 shown in FIG. 4), and (ii) attach to the above-described bracket (e.g., exemplary bracket 60 shown in FIGS. 6A-6B) along opposing ends of the rod.

Exemplary rod 50 has dimensions suitable for supporting a roll of sleeves within a volume of space located between an upper surface 67 of central member 61 and opposing inner surfaces 65 and 66 of end members 62 and 63 respectively (see, FIGS. 6A-6B). For example, when sleeve width w is about 3.0 in (7.6 cm) and end members 62 and 63 are spaced from one another by about 3.2 in (8.1 cm), exemplary rod 50 may have a rod length of about 3.3 in (8.4 cm).

Exemplary rod 50 may comprise a variety of materials. Suitable materials include, but are not limited to, metals such as steel or stainless steel, and polymeric materials such as the above-described film-forming and thermoformable materials. Desirably, exemplary rod 50 comprises a polymeric rod comprising an ABS copolymer.

E. Attachment Members

As discussed above, the articles of the present invention may further comprise one or more attachment members such as attachment members 40 shown in FIG. 3. Exemplary attachment members 40 are operatively adapted to attach housing 30 (or a bracket contained therein) to another object, such as a portion of stethoscope 10, namely, stethoscope tubing 12 as shown in FIG. 3. Attachment members 40 may extend from an outer surface of housing 30 or may be an integral component of a bracket contained within housing 30 as shown in FIGS. 6A-6B (see, attachment members 68 extending from bracket 60).

Attachment members 40 and 68 may comprise any device component capable of connecting a housing (e.g., housing 30), bracket (e.g., bracket 60), sleeve (e.g., sleeve 20), or roll of sleeves (e.g., roll of sleeves 200) to another object such as a portion of a stethoscope (e.g., stethoscope tubing 12). Suitable attachment members include, but are not limited to, plastic clamps such as attachment members 68 extending from bracket 60, hook and loop material, and an adhesive (e.g., a pressure sensitive adhesive).

Attachment members 40 and 68 may have any size and/or dimensions as long as the attachment members are capable of connecting to another object such as a portion of a stethoscope (e.g., stethoscope tubing 12). Typically, attachment members 40 and 68 are dimensioned so as to clamp onto and/or surround another object such as the tubing of a stethoscope (e.g., stethoscope tubing 12).

Exemplary attachment members 40 and 68 may comprise a variety of materials. Suitable materials include, but are not limited to, metals such as steel or stainless steel, and polymeric materials such as the above-described film-forming and thermoformable materials. Desirably, exemplary attachment members 40 and 68 comprise a thermoformable material such as polypropylene or an ABS copolymer.

II. Methods of Making Articles

The present invention is further directed to methods of making articles. In one exemplary embodiment of the present invention, the method of making an article comprises forming a sleeve comprising two film portions (e.g., film portions 22 and 28) joined to one another (i) along at least one edge extending along a sleeve length (e.g., edge 33 or 34) and (ii) along opposite edges extending along a sleeve width (e.g., edges 27 and 29), and providing a sleeve opening (e.g., sleeve opening 23) through one of the two film portions (e.g., film portion 22) so that the sleeve opening extends across the sleeve width and is positioned at a location along the sleeve length between the opposite edges, the sleeve opening being sized so that at least a portion of an insertable object, such as a stethoscope bell (e.g., stethoscope bell 13) can extend therethrough and into a cavity (e.g., cavity 32) surrounded by the two film portions. As discussed above, the two film portions (e.g., film portions 22 and 28) may be separate films joined to one another along opposite edges or may be a single tubular film that is flattened, and subsequently cut so as to form a sleeve opening through one of the two film portions.

In a further exemplary embodiment of the present invention, the method of making an article comprises forming a roll of sleeves (e.g., roll of sleeves 200) comprising two or more sleeves (e.g., sleeves 201 and 202) that are (i) connected to one another, and (ii) separated from one another via at least one line of perforations that enables the two or more sleeves to be separated from one another along the at least one line of perforations, each sleeve having a sleeve opening positioned along a length of the sleeve, the sleeve opening providing access to a cavity within the sleeve, the cavity being operatively adapted to surround at least a portion of an insertable object, such as a stethoscope bell. In this embodiment, the film material used to form the roll of sleeves may be two film portions (e.g., film portions 22 and 28) joined to one another along opposite edges or may be a single tubular film that is flattened, and subsequently cut so as to form a sleeve opening through one of the two film portions and lines of perforations along the roll of sleeves.

The methods of making an article may further comprise one or more of the following method steps: forming a tubular film; bonding one or more edges of a film sheet to one another to form a tubular film; bonding one or more edges of two separate film sheets to one another to form a tubular film; forming a line of perforations within attached film portions or a flattened tubular film; adding a colorant to a polymer melt prior to forming a film or tubular film; printing a colorant onto a surface of a film portion; unrolling attached film portions or a flattened tubular film from a roll; taking-up a roll of sleeves on a rod or mandrel; inserting a rod through a roll of sleeves; forming a bracket (e.g., molding a bracket); attaching a roll of sleeves to a bracket via a rod; thermoforming material to be used to form a housing (e.g., extruding a film to be used to form the housing); cutting the thermoformed housing material to form a desired shape/configuration; positioning a roll of sleeves (with or without bracket and rod) within the thermoformed housing material; positioning attachment members of a bracket through slots within the thermoformed housing material; folding and bonding the thermoformed housing material with a roll of sleeves contained therein so that a portion of a sleeve extends through a sleeve slot in the housing; and attaching the article to another object, such as a stethoscope.

Any of the above-described individual components used to form the articles of the present invention may be formed using conventional methods. For example, all of the above-mentioned possible components including, but not limited to, sleeve 20, roll of sleeves 200, housing 30, attachment members 40, rod 50, and bracket 60 may be formed from any of the film-forming or thermoformable materials described above. The film-forming or thermoformable materials can be molded or shaped using any conventional molding technique.

Any films or film-like components including, but not limited to, sleeve 20, roll of sleeves 200, and housing 30, may be forming via any film-forming process including, but not limited to, a film extrusion process, a film-blowing process, etc.

Thermoformed parts, films and/or fabric layers may be joined to one another using any conventional bonding technique including, but not limited to, thermal bonding processes, adhesive bonding, mechanical bonding (e.g., ultrasonic welding or hook and loop material), etc. In one exemplary embodiment of the present invention, housing 30 is formed from a polyvinyl chloride (PVC) film and is thermally bonded to itself so as to form a three-dimensional housing capable of encompassing a sleeve or roll of sleeves using a conventional bonding apparatus (e.g., an ultrasound welder).

In one desired embodiment, the article of the present invention is formed from the following materials: EMA film (e.g., roll of sleeves 200); PVC film (e.g., housing 30); and an ABS copolymer (e.g., bracket 60 with attachment members 68 and rod 50).

III. Methods of Using Articles

The present invention is even further directed to methods of using articles of the present invention. The articles of the present invention are particularly useful in the medical industry. For example, The articles of the present invention may be used to temporarily cover or protect a piece of medical equipment, such as a stethoscope bell. In one exemplary embodiment of the present invention, the method of using an article comprises inserting at least a portion of a medical instrument within a cavity of a sleeve while the sleeve is connected to a roll of sleeves so as to form a covered medical instrument; utilizing the covered medical instrument for an intended purpose; and, after the utilizing step, separating the sleeve from the roll of sleeves by tearing along at least one line of perforations. In the above-described exemplary method, the medical instrument may comprise a stethoscope, the portion of a medical instrument may comprise a stethoscope bell, and the intended purpose may be detecting a heart beat.

In one desired embodiment of the present invention, the method comprises providing an article such as one of the above-described articles; attaching the article to a stethoscope; positioning a stethoscope bell within a first sleeve so as to form a covered stethoscope bell; and contacting a first patient with a portion of the covered stethoscope bell. The exemplary method may further comprise removing the stethoscope bell from the first sleeve; optionally removing the first sleeve from a roll of sleeves; positioning the stethoscope bell within a second sleeve so as to form a covered stethoscope bell; and contacting a second patient with a portion of the covered stethoscope bell.

While the specification has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. An article comprising:
   a roll of sleeves comprising two or more sleeves that are (i) connected to one another, and (ii) separated from one another via at least one line of perforations that enables the two or more sleeves to be separated from one another along the at least one line of perforations, each sleeve having a sleeve opening that (1) is substantially parallel to (i) the at least one line of perforations and (ii) opposite end edges of a given sleeve, and (2) is positioned along a length of the sleeve at a location that is a distance from (i) the at least one line of perforations and (ii) the opposite end edges of a given sleeve, said sleeve opening providing access to a cavity within the sleeve, said cavity being operatively adapted to surround at least a portion of an insertable object, said roll of sleeves having an axis of rotation (i) extending through said roll of sleeves and (ii) parallel to the at least one line of perforations;
   a housing sized and configured so as to encompass and enclose the roll of sleeves within said housing, said housing comprising a first slot sized so that at least an end portion of a sleeve can extend therethrough;
   a bracket for suspending the roll of sleeves within the housing;
   a rod operatively adapted to (i) extend through the roll of sleeves along the axis of rotation of the roll of sleeves, and (ii) attach to said bracket along opposing ends of said rod; and
   one or more attachment members operatively adapted to attach the roll of sleeves to a stethoscope, wherein said one or more attachment members (i) extend from and are integrally connected to said bracket, and (ii) extend through second slots within said housing.

2. The article of claim 1, wherein each sleeve comprises:
   two film portions joined to one another along at least one edge extending along a sleeve length, said sleeve opening being sized so that at least a portion of a stethoscope bell can extend therethrough and into the cavity surrounded by the two film portions.

3. The article of claim 2, wherein said two film portions are joined to one another along opposite edges extending along the sleeve width.

4. The article of claim 3, wherein said location is within an upper half of a given sleeve, said upper half being positioned between a midpoint along the given sleeve and an end edge closest to said roll of sleeves.

5. The article of claim 2, wherein said two film portions are transparent or translucent.

6. A stethoscope cover assembly comprising:
the article of claim 1; and
a stethoscope.

7. The stethoscope cover assembly of claim 6, wherein the article is attached to the stethoscope.

8. A method of using the article of claim 1, said method comprising:
inserting at least a portion of a medical instrument within a cavity of a sleeve while the sleeve is connected to the roll of sleeves so as to form a covered medical instrument;
utilizing the covered medical instrument for an intended purpose while the sleeve is connected to the roll of sleeves; and
after said utilizing step, separating the sleeve from the roll of sleeves by tearing along the at least one line of perforations.

9. The method of claim 8, wherein the medical instrument is a stethoscope, and the portion of the medical instrument inserted within the cavity of the sleeve is a stethoscope bell.

10. The article of claim 1 attached to a stethoscope.

* * * * *